United States Patent
Jackson

(10) Patent No.: US 9,907,937 B2
(45) Date of Patent: Mar. 6, 2018

(54) COATED TISSUE EXPANDER

(71) Applicant: OXTEX LIMITED, Oxford (GB)

(72) Inventor: David Edward Jackson, Wallingford (GB)

(73) Assignee: OXTEX LIMITED, Oxford (GB)

( * ) Notice: Subject to any disclaimer, the term of this patent is extended or adjusted under 35 U.S.C. 154(b) by 205 days.

(21) Appl. No.: 14/912,264

(22) PCT Filed: Aug. 13, 2014

(86) PCT No.: PCT/GB2014/052483
§ 371 (c)(1),
(2) Date: Feb. 16, 2016

(87) PCT Pub. No.: WO2015/022534
PCT Pub. Date: Feb. 19, 2015

(65) Prior Publication Data
US 2016/0199144 A1    Jul. 14, 2016

(30) Foreign Application Priority Data
Aug. 16, 2013   (GB) .................................. 1314707.9

(51) Int. Cl.
*A61M 29/00* (2006.01)
*A61M 29/02* (2006.01)
(Continued)

(52) U.S. Cl.
CPC .............. *A61M 29/02* (2013.01); *A61B 90/02* (2016.02); *A61B 2017/00526* (2013.01);
(Continued)

(58) Field of Classification Search
CPC ..... A61M 29/02; A61M 29/00; A61F 2/0059; A61F 2210/0061; A61F 2250/0004;
(Continued)

(56) References Cited

U.S. PATENT DOCUMENTS 4,574,780 A * 3/1986 Manders ................ A61B 90/02
128/898
4,615,704 A * 10/1986 Frisch .................... A61B 90/02
128/899
(Continued)

FOREIGN PATENT DOCUMENTS

CN    2272760    1/1998
CN    2440529    8/2001
(Continued)

OTHER PUBLICATIONS

International Preliminary Report on Patentability issued by the International Bureau of WIPO from PCT Application No. PCT/GB2014/052483 dated Feb. 16, 2016, 7 pages.
(Continued)

*Primary Examiner* — Katrina Stransky
(74) *Attorney, Agent, or Firm* — Meunier Carlin & Curfman LLC

(57) ABSTRACT

The present invention provides a tissue expander (10) comprising a self-inflating core (12) having a non-inflated state and an inflated state and a coating (14) surrounding said core (12), in which said core (12) comprises a compacted material having a central portion (16) of a first, higher, (average) density D and a peripheral portion (18) of a second, lower, (average) density d, a border (19) between said central portion (16) and said peripheral portion (18) and wherein said coating (14) includes a plurality of first and/or second apertures (20, 22) through said coating (14). It also provides a method of manufacturing the tissue expander (10). The arrangement is such as to allow for the controlled ingress of water into the expandable core (12) which allows for the control of the delay before expansion and the rate of expansion once initiated.

20 Claims, 3 Drawing Sheets

(51) Int. Cl.
*A61B 90/00* (2016.01)
*A61B 17/00* (2006.01)

(52) U.S. Cl.
CPC .............. *A61B 2017/00792* (2013.01); *A61B 2017/00898* (2013.01); *A61B 2017/00942* (2013.01)

(58) Field of Classification Search
CPC A61B 2017/00526; A61B 2017/00792; A61B 2017/00898; A61B 2017/00942; A61B 90/02; A61B 90/00; A61B 19/24; A61L 31/10; A61L 31/145; A61L 31/146
See application file for complete search history.

(56) References Cited

U.S. PATENT DOCUMENTS

| | | | | |
|---|---|---|---|---|
| 4,651,717 | A * | 3/1987 | Jakubczak | A61B 90/02 |
| | | | | 128/899 |
| 5,005,591 | A | 4/1991 | Austad | |
| 5,496,368 | A | 3/1996 | Wiese | |
| 6,228,116 | B1 * | 5/2001 | Ledergerber | A61F 2/0077 |
| | | | | 623/8 |
| 2002/0091443 | A1 | 7/2002 | Yoon | |
| 2006/0155163 | A1 * | 7/2006 | Yachia | A61B 5/205 |
| | | | | 600/29 |
| 2009/0048683 | A1 * | 2/2009 | Morris | A61B 17/56 |
| | | | | 623/23.48 |
| 2010/0049316 | A1 * | 2/2010 | Schuessler | A61F 2/12 |
| | | | | 623/8 |
| 2010/0114312 | A1 * | 5/2010 | Glicksman | A61F 2/12 |
| | | | | 623/11.11 |
| 2011/0077682 | A1 * | 3/2011 | Gregory | A61F 13/00008 |
| | | | | 606/213 |
| 2011/0112383 | A1 | 5/2011 | Voss et al. | |
| 2011/0270391 | A1 * | 11/2011 | Chitre | A61F 2/12 |
| | | | | 623/8 |
| 2012/0265165 | A1 * | 10/2012 | Bucknall | A61L 27/26 |
| | | | | 604/500 |
| 2013/0079807 | A1 * | 3/2013 | Korman | A61B 90/02 |
| | | | | 606/192 |
| 2014/0100596 | A1 * | 4/2014 | Rudman | A61M 29/02 |
| | | | | 606/195 |
| 2014/0142523 | A1 * | 5/2014 | Steinbaugh | A61F 13/00008 |
| | | | | 604/304 |
| 2014/0288646 | A1 * | 9/2014 | Khouri | A61F 13/145 |
| | | | | 623/8 |
| 2015/0272723 | A1 * | 10/2015 | Hristov | A61F 2/12 |
| | | | | 623/8 |
| 2015/0351900 | A1 * | 12/2015 | Glicksman | A61F 2/12 |
| | | | | 623/8 |
| 2016/0250017 | A1 * | 9/2016 | McClellan | A61F 2/12 |
| | | | | 623/8 |
| 2017/0259049 | A1 * | 9/2017 | Gregory | A61F 13/00008 |

FOREIGN PATENT DOCUMENTS

| | | |
|---|---|---|
| CN | 102639163 | 8/2012 |
| EP | 2470233 | 7/2012 |
| GB | 2139898 A | 11/1984 |
| WO | 2011051731 A2 | 5/2011 |

OTHER PUBLICATIONS

First Office Action and Search Report issued by the State Intellectual Property Office of the People's Republic of China in connection with Chinese Application No. 201480045449.8 dated May 3, 2017.
International Search Report and Written Opinion of the International Searching Authority from PCT Application No. PCT/GB2014/052483, dated Oct. 29, 2014, 10 pages.
Search Report of the GB Intellectual Property Office from Application No. GB1314707.9, dated Feb. 12, 2014, 4 pages.
Examination Report of the GB Intellectual Property Office from Application No. GB1314707.9, dated Oct. 5, 2015, 2 pages.

* cited by examiner

COATED TISSUE EXPANDER

The present invention relates to expandable components and relates particularly but not exclusively to components known as tissue expanders. Such expanders are used by medical, veterinary and dental staff to cause the expansion of patient tissue in advance of corrective or supplemental surgery and generally are such as to have a controlled rate of expansion and may also be configured to have a delayed expansion capability.

Tissue expanders are now a key component in reconstructive plastic surgery and are used for example in the treatment of congenital abnormalities and acquired defects.

One known form of tissue expander is described in EP10776126 and from which it will be appreciated that they generally comprise a dried then compressed material which, when re-hydrated will expand to re-gain any height lost during compression. The rate of expansion may be controlled by coating the expandable material in a bio-degradable coating which, upon insertion in the patient, will degrade upon exposure to moisture and then allow the moisture to access the expandable de-hydrated material such as to hydrate it and cause it to expand. An alternative approach is to make the expandable material as an Inter-penetrating Network of bio-degradable material and expandable material which, in combination, provide the delay and the expansion. The expandable material can be formed from a number of materials but new forms of hydrogel (a gel in which water is the dispersion medium) are of particular use in such applications Such expanders are generally known as "self-inflating tissue expanders".

Whilst the above-mentioned arrangement is able to offer some degree of control over the delay and the rate of expansion, it has been found that still further control is required in order to provide an acceptable product. In addition, it is desirable to be able to provide an arrangement in which the delay and indeed the rate of expansion can be easily altered in order to accommodate particular or individual requirements without having to alter the basic structure or core manufacturing process.

It is an object of the present invention to provide a tissue expander which improves on those already known and may able to offer at least some degree of control over one or other of the delay or the rate of expansion and which might also be more easily altered to accommodate differing requirements for delay and expansion rate.

Accordingly, according to a first aspect of the present invention, there is provided a tissue expander comprising a self-inflating core having a non-inflated state and an inflated state and a coating surrounding said core, in which said core comprises a compacted material having a central portion of a first, higher, (average) density D and a peripheral portion of a second, lower, (average) density d, a border between said central portion and said peripheral portion and wherein said coating includes a plurality of first and/or second apertures through said coating.

Preferably, the arrangement includes one or more first apertures radially spaced from said border and radially inwards thereof.

Additionally or alternatively the arrangement may include a plurality of second apertures positioned on said border.

Additionally or alternatively the arrangement may include a plurality a plurality of third apertures radially spaced from said border and radially inwards thereof.

Advantageously, said first apertures may be circumferentially spaced around a central axis X of said tissue expander.

Advantageously said second apertures are circumferentially spaced around a central axis X of said tissue expander.

Advantageously, said third apertures are circumferentially spaced around a central axis X of said tissue expander.

Preferably, said expandable core includes an upper surface and a lower surface and wherein a plurality of said apertures are provided through said coating adjacent one or more of said upper and lower surfaces.

Advantageously, the arrangement includes a semi-permeable barrier material within one or more of said apertures. Said barrier material may be used for controlling the rate of water ingress.

Advantageously, said core includes edges or corners and wherein said coating has a greater thickness adjacent said edges than at other portions.

In a preferred arrangement said core includes first edges having a radius of curvature R and wherein said coating has second edges adjacent said first edges and having a radius of curvature r less than said first radius of curvature R.

Preferably, said core comprises a self-inflating polymer, although other self-inflating materials can be used.

According to a second aspect of the present invention, there is provided a method of manufacturing a tissue expander comprising the steps of:

a) selecting a self-inflating hydrophilic core material;

b) forming said selected material to a given height H and width W;

c) drying said core material;

d) compacting said core material with a force F sufficient to overcome slipping friction and reducing the height H thereof whilst increasing the width W thereof;

e) compacting the central region (16) to a first, higher, (average) density D and a peripheral region (18) to a second, lower, (average) density d, and creating a border (19) between said central region (16) and said peripheral region (18);

f) coating said core (12) with a coating (14); and g) providing a plurality of first and/or second apertures (20, 22) through said coating (14);

wherein the force F required to overcome the slipping friction is determined from F=2k exp(2μ/h (b/2−x)), and wherein the force required to overcome the slipping friction is determined form the following formula:

$$F = 2k\left(1 + \left(\frac{\frac{b}{2} - x}{h}\right)\right)$$

Where: F=force, μ=friction, k=shear yield stress, h=height, b/2=radius and x=distance from center.

Preferably, the method includes the step of forming the core material with edges having a radius of curvature R and coating said coating onto the core by moulding said coating around the core.

Advantageously, the method includes the step of forming the coating material with edges adjacent the edges of the core and having a radii of curvature r which is less than the radii of curvature R of the edges of the core.

Preferably, the method includes the step of providing the coating in the form of a water impermeable coating.

Advantageously, the method includes the further steps of providing one or more apertures through said coating.

The present invention will now be more particularly described by way of example only with reference to the accompanying drawings, in which.

The present invention may employ a self-inflating polymer gel. The self-inflating polymer network of the present invention may be based on a hydrophilic polymer network which is capable of absorbing water without dissolution. The hydrophilic properties are provided by functional groups on the polymer(s) (e.g. hydroxyl, carboxyl or amide functional groups). Preferably the self-inflating polymer network comprises at least one monomer containing —COOH, >C=0, —OH, or —NH$^2$ groups. The resistance to dissolution is a result of the presence of structural cross-linkages, crystalline regions or entanglements. Such materials are typically termed "hydrogels". The hydrogel contains two components, namely the polymer network (i.e. the gel), which is constant in quantity, and a variable aqueous component. In the anhydrous state (prior to implantation), the material is normally referred to as a xerogel. The anhydrous material is hygroscopic and absorbs/adsorbs water from its local environment to hydrate the network. The self-inflating polymer network may swell to many times its dry mass. Typically, the aqueous phase comprises 90% or more, preferably 95% or more of the total mass of the self-inflating polymer network at equilibrium. The expansion of the self-inflating polymer network is driven by the diffusion of water molecules into the polymer network which is due to osmosis and the interaction between the polymer and water molecules in order to reduce the Gibbs free energy of the system when the polymer is introduced into an aqueous environment, i.e. from tissue fluid in vivo. The self-inflating polymer network approaches its equilibrium state when the driving force for the mixing between the polymer species and the solvent is balanced by the restoring force of the chains in the network due to the elasticity of polymer network. Whilst there are number of self-inflating polymers that could be used hydrogels are the most suited to medical applications. It is preferable that the hydrogel comprises functional groups on the polymer (e.g. hydroxyl, carboxyl or amide functional groups or others which provide the hydrophilic properties thereof. The expansion of the above self-inflating polymer is driven by the diffusion of water molecules into the polymer network which is due to osmosis and the interaction between the polymer and water molecules in order to reduce the Gibbs free energy of the system when the polymer is introduced into an aqueous environment, such as may be experienced when inserted within a human or animal body.

The self-inflating polymer network approaches its equilibrium state when the driving forces for the mixing between any polymer species and any solvent is balanced by the restoring force of the chains in the network due to the elasticity of the polymer network itself.

Figures 1, 2, 3:
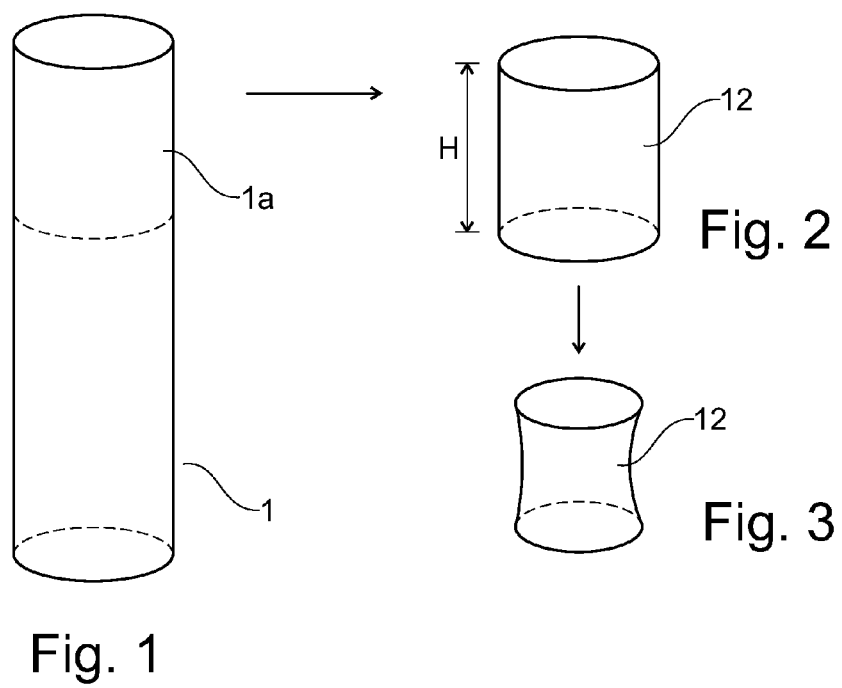
FIG. 1 is a diagrammatic representation of a rod of preformed expandable material.
FIG. 2 is a view of a short length of the material shown in FIG. 1 prior to a drying step.
FIG. 3 is a view of the material of FIG. 2 after a drying or de-hydration step has been performed thereon.

A first manufacturing process which may be employed in the manufacture of the present product is illustrated in FIGS. 1 to 3, in which a partially hydrated self-inflating polymer gel is formed into a pre-determined shape 1, a portion of which 1a is cut therefrom to form the shorter portion 12 or core shown first in FIG. 2. The Height H of the core 12 of FIG. 2 is selected to be sufficient to provide the height H$^4$ required in a finished expander after expansion has taken place. It will, therefore, be appreciated that height H may be varied to suit different requirements. The self-inflating polymer is hydrophilic and, therefore, able to absorb water without dissolution and it is this property that is employed to advantage in the present invention.

Figure 6:
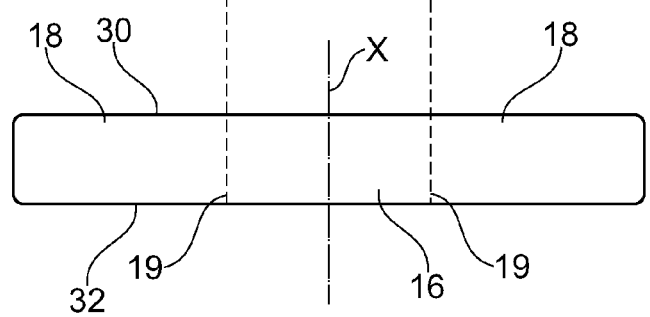
FIG. 6 is a cross-sectional view of the compacted core of the present invention and illustrates the position of a barrier between a central portion and a peripheral portion thereof.
Figure 7:
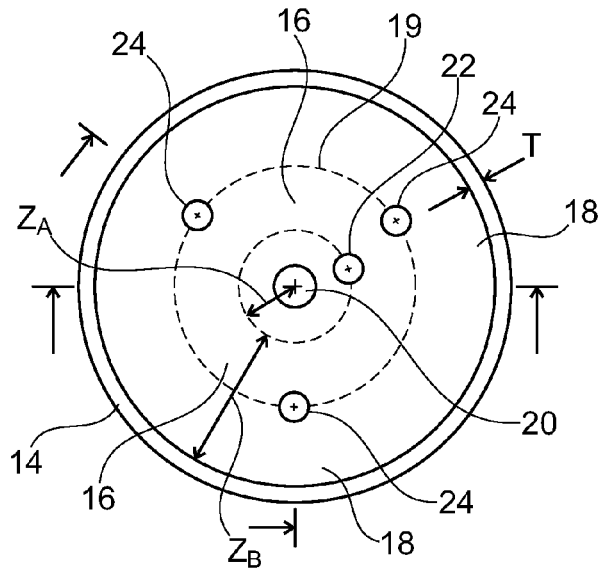
FIG. 7 is a plan view of a the core of FIG. 6 when coated with a coating and provided with apertures therethrough.
Figure 8:
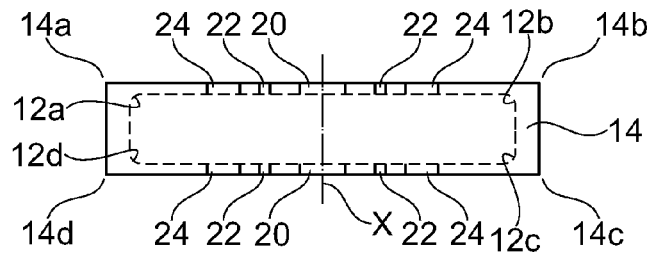
FIG. 8 is a cross-sectional view of the arrangement o FIG. 7.

The core 12 of FIG. 2 is then dried such as to remove the pre-hydration moisture therefrom and produce the component of FIG. 3 which is in the state required for compression forming into the shaped core 12 shown more specifically in FIGS. 6 to 8. It will be appreciated that the partial pre-hydration step will make it easier to cut into a desired shape but that this step may be eliminated if the machinery is available to simply cut the de-hydrated starting material 1 to the desired length. This would also allow for the elimination of the de-hydration step between FIGS. 2 and 3.

Figure 4:
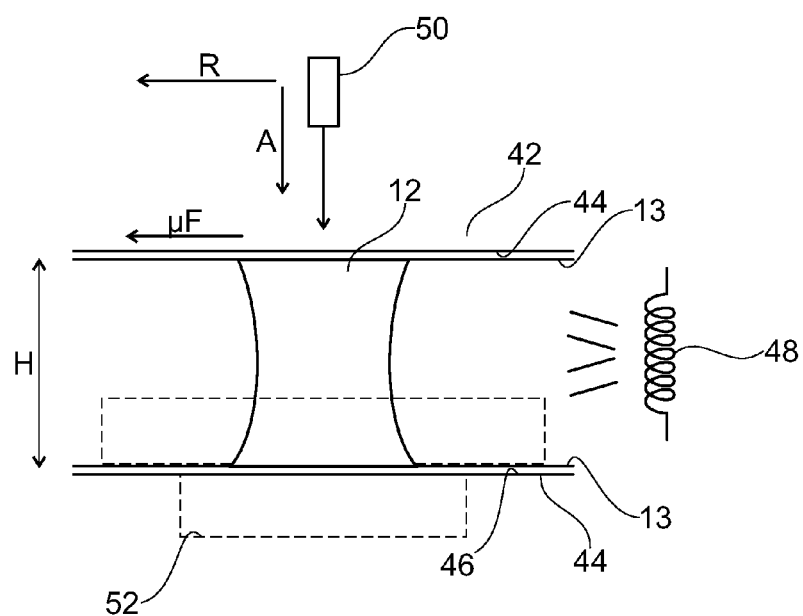
FIG. 4 is a diagrammatic representation of a compaction apparatus and illustrates the shape of the material of FIG. 3 both before and after compaction.

Compression of the core 12 is illustrated diagrammatically in FIG. 4 and from which it will be appreciated that the dried un-compacted core 12 is placed between two compression members 40, 42 having confronting surfaces 44, 46 which, in operation, are preferably shielded from direct contact the core 12 by means of an interlayer 13 in the form of, for example, a layer of silicone or other such suitable inert material. A heater and compression ram, shown schematically at 48, 50 respectively are used to heat and compress the core as detailed below. Compression is done by applying heat and pressure to the core (typically applied in one direction or plane so as to reduce the height H) to provide a subsequent anisotropic expansion principally in the direction of compression. The combination of heat at around or above the glass transition temperature (T[g]) of the polymer and pressure causes the molecular chains to realign. Clearly heating should be lower than the degradation temperature of the polymer. The core 12 may be formed between flat surfaces in which case compaction creates a generally circular lozenge shaped component or it may be formed into a mould shown in dotted format at 52 in FIG. 4.

The compression step reduces the height H of the core whilst increasing the width W, as shown in FIG. 4. The loss in height H corresponds to the increase in height H when the core is re-hydrated in use and, hence, the starting height H of the pre-compressed core 12 and the compressed height H° may be adjusted as required in order to ensure the desired expansion is achieved. During expansion the width W will decrease whilst the height H will increase. The compression step itself places the core 12 under a number of forces which include both axial and radial forces shown schematically by arrows A and R. the axial force A is that which is applied to reduce the height H and is directly related to the degree of compression but the radial force R has a component which depends on the frictional properties at the junction of the core material and the confronting surfaces 44, 46. In essence, the greater the degree of friction (µF) the greater the element of radial force R required to compress the core 12.

Figure 5:
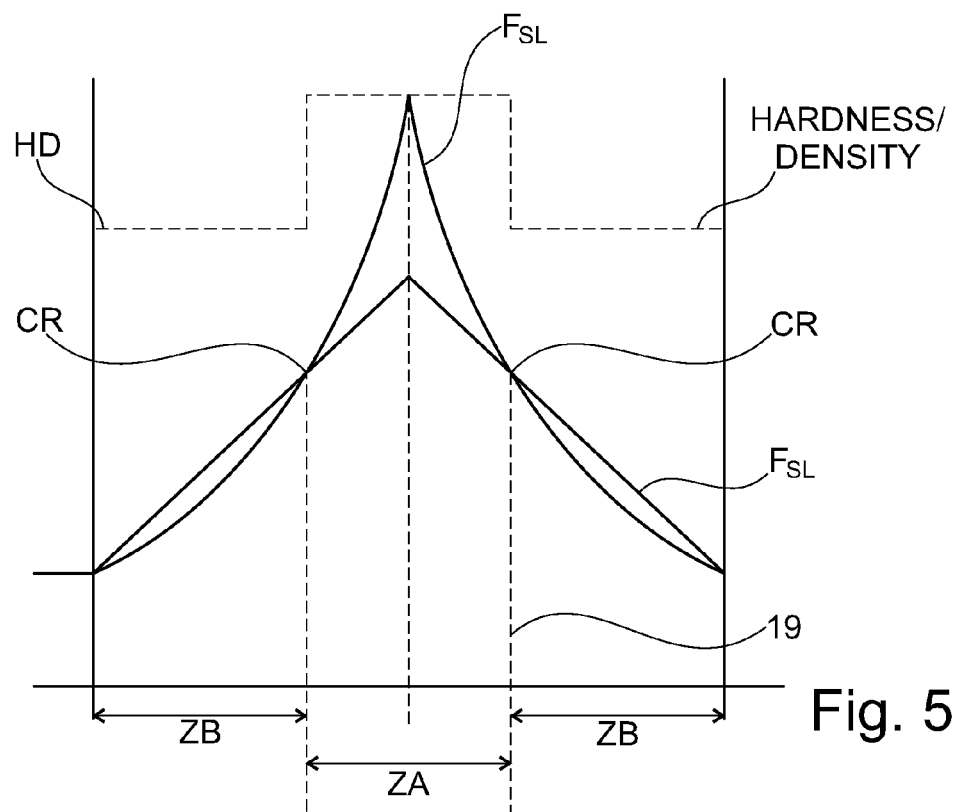
FIG. 5 is a graph illustrating the properties of the compacted core produced by the compaction process associated with FIG. 4.

It has been found that the above-discussed compression process imparts particular properties into the compacted core 12. These properties may be exploited in the present invention and are described in detail with reference to FIGS. 5 and 6. FIG. 5 is a graph illustrating two properties of the core 12 at various radial positions across the core that are induced and which may be modified by altering the axial compression load and the degree of friction μ at the interface discussed above. The graph of FIG. 5 illustrates the variation across the core in sticking friction $F_{ST}$ and slipping friction $F_{SL}$ where the magnitude of the sticking friction $F_{ST}$ is dependent upon the axial load applied in the direction of arrow F and the slipping friction $F_{SL}$ is related to the coefficient of friction μ at the interface. The sticking friction $F_{ST}$ varies linearly from a maximum at the centre of the core 12 to a minimum at the outer periphery 12a thereof. The slipping friction $F_{SL}$ varies in a non-linear manner from a maximum at the centre of the core 12 to a minimum at the outer periphery 12a thereof.

The force required to overcome the slipping friction is determined form the following formula:

$$F = 2k \exp(2\mu/h(b/2 - x))$$

The force required to overcome the sticking friction is determined by the following formula:

$$F = 2k\left(1 + \left(\frac{\frac{b}{2} - x}{h}\right)\right)$$

Where: F=force, μ=friction, k=shear yield stress, h=height, b/2=radius and x=distance from centre.

As shown in FIG. 5, there is a point of cross-over CR of the magnitude of the frictions and it is this cross-over point which defines a border 19 between what are described herein as a central portion 16 and a peripheral portion 18 if the core 12 itself. The inter-relationship between the magnitudes of slipping friction and sticking friction results in the central portion 16 having a higher (average) hardness and density than the outer peripheral portion 18 and the defining of the border 19 which, it has been found is the point of initiation of any subsequent expansion after hydration. This understanding has been exploited in the present invention such as to create a self-inflating tissue expander 10 in which a controllable delay in expansion may be designed into the finished article and which may be tailored such as to set both the degree of delay and the rate of expansion after insertion into the hydrating medium.

Figure 9:
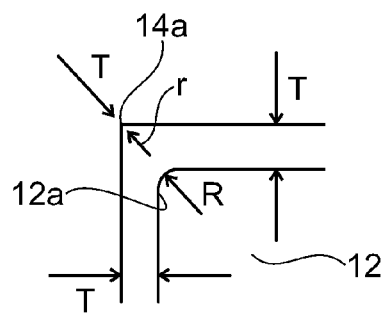
FIG. 9 is a detailed cross-sectional view of a corner portion of FIG. 8 and illustrates the difference between the radii R of the corner of the core and the radii r of the corner of the coating.

Reference is now made to FIGS. 7 to 9 which illustrate the finished product in more detail and from which it will be appreciated that an outer coating 14 having a thickness T which is applied to the core of FIG. 6 in order to provide a barrier to water impregnation. Such a layer may comprise Silicone as this will expand with the core 12 but other materials such as polyurethane may also be used. In essence, the coating 14 must resist the passage of water therethrough but be sufficiently flexible as to accommodate the subsequent change in shape and dimension of the core as it expands. Preferably the coating comprises a water impermeable material. A plurality of apertures 20, 22, 24 may be provided in the coating 14 such as to extend through the coating 14 and to one or other or both of the upper and lower surfaces 30, 32 of the core 14 itself. These apertures 20, 22, 24 provide a route through which water can reach the core 12 and may be plugged with a semi-permeable barrier material 26 so as to control the rate of water ingress. The properties of the semi-permeable barrier material 26 may be varied between finished articles such as to provide a more tailored product where the rate of fluid absorption can be pre-defined or they may be set as a constant between finished products if so desired. The expansion of the core 12 initiates at the barrier 19 and, thus, one can vary the delay between insertion and expansion by varying the distance $Z_A$, $Z_B$ of any apertures 20, 24 from the barrier 19. In operation, water will take some time to penetrate through the apertures and then track towards the barrier 19 and, hence, the greater the distances $Z_A$, $Z_B$ the greater the delay in expansion. Clearly, apertures can be placed in association with the central region and/or the peripheral region and may even be placed immediately above the barrier 19 as shown by apertures 22 if it is desired to have zero delay in expansion. The size and/or number of the holes 20, 22, 24 may be altered so as to increase or decrease the rate of expansion once it has been initiated.

From the above, it will be appreciated that the present invention is able to take control over the delay before expansion and the rate of expansion once initiated by varying the position, number and size of the holes and the permeability of the holes by the provision of plugs of defined permeability or the elimination thereof as desired. Further, the surgeon may be able to modify the final produce before insertion by simply filling in holes or removing already inserted plugs such as to alter the rate of expansion. Still further, the surgeon may be able to increase the number of holes and/or the position of added holes should that be desired. It will also be appreciated that the coating 14 is in intimate contact with the core 12 which ensures that any fluid which is passed through to the core is channelled in a controlled manner to the barrier region 19 such as to ensure consistency in the delay before expansion takes place.

FIG. 7 provides a cross-sectional view of the tissue expander 10 of FIG. 7 and illustrates a plurality of holes in fluid communication with both the upper and lower surfaces 30, 32 of the core itself. The provision of holes on both sides, whilst not being essential, will help ensure the expansion takes place evenly on both sides and may also ensure a more rapid and complete expansion. The holes may be evenly or unevenly spaced and may be positioned in circumferentially spaced manner around a central axis X if the core. In certain arrangements a central hole may be provided on the axis X which may be used individually or in combination with other holes.

FIG. 8 illustrates the detail associated with the corners of the expander 10 and from which it will be appreciated that the compression of the core 12 will create a lozenge shaped component having corners 14a, 14b, 14c, 14d with a radius of curvature R. it has been found that the coating 14 when applied by dip coasting techniques can be thinner at the corners than might be desirable and premature rupturing of the coating 14 can occur at these positions. In order to solve this problem, the present invention proposes an arrangement in which the coating is applied such as to have a thicker coating thickness T at the corners. Such an arrangement can be achieved by injection moulding the coating in a mould containing the compressed core 12 in a mould which has a defined shape with corners adjacent the corners 12a-12d of the core which are of a lesser radius r than radius R. the mould radius r will then translate into a coating radius r at the corners 14a-14d which is less than the radius R, thus creating an increased local thickness T at the corners. This extra thickness at the crucial corner positions will ensure that premature rupturing during expansion is substantially eliminated. A similar issue may arise in connection with core material 12 which is compressed within the mould arrangement shown schematically at 52 in FIG. 4. An alternative solution may present itself in the modification of the corners of the implant 12 such that the radii R associated therewith are sufficiently large as to allow for the deposition of a coating thickness sufficient to survive any expansion of the core without rupturing. An optional method coating may comprise dip coating so long as the thickness of the coating at the corners 12a-12d is sufficient as to retain the integrity of the coating during any subsequent expansion step. If dipping is used, the corners may be rounded with a greater radius of curvature R than might be needed in the moulded arrangement discussed in reference to FIGS. 8 and 9.

The present invention also provides a method of manufacturing a tissue expander 10 as described above including the steps of first selecting a hydrated self-inflating hydrophilic core material and then forming said selected material to a given height H and width W by, for example, cutting from a length thereof. The cut length is then dried to remove as much moisture as possible which will cause the material to shrink in height H and width W which is required prior to the next step which is compaction. The core 12 is then compacted between, for example, the compression members 42, 44 of FIG. 4 such as to reduce the height H thereof whilst increasing the width W such as to produce a compacted core 12 in the shape of a lozenge which, by virtue of the compaction process will have an inner region of a first, higher, (average) hardness/density HD and a peripheral region 18 of a second, lower, (average) hardness/density hd, a border 19 between said central region 16 and said peripheral region 18.

The compaction process itself is controllable in as much as the rate of compaction, the temperature and the degree of friction can be controlled. Compression rates will depend on the materials being used and the glass transition temperature thereof as well as the degree of heating undertaken during pressing. The degree of friction between the compressing core 12 and the compression members 42, 44 is also important and can be controlled by the application of the interlayer of silicone sheet 13. The sliding properties of the sheet helps reduce the slipping friction μF which is present when the core is squashed radially outwardly and alteration of the friction will affect the profile of the slope shown in FIG. 5. It will, therefore, be appreciated that one may alter the point at which the slipping friction and sticking friction profiles of FIG. 5 cross each other and, as this crossing point defines the barrier 19, it is possible to define the position of the barrier 19 in any formed core This is important as being able to define the position of the barrier 19 allows one to alter the position of the expansion initiation point as such takes place from the barrier portion 19 itself. Also, being able to control the position of the barrier portion 19 and ensure it is at a set position will allow one to accurately position any apertures 20, 22, 24 relative thereto such as to accurately set the delay before expansion takes place.

The next step comprises coating the core 12 with a protective coating designed to control ingress of water into the core 12. Whilst a number of coatings 14 can be used, it has been found that a Silicone 13 layer lends itself to the present application as it has a good degree of flexibility, accommodates the desired expansion of the core 12 and is able to accommodate the formation of apertures 20, 22 as and where desired. Whilst the coating 14 may be applied by dip coating, the present applicants have realised that dip coating often results in a thinning of the coating at the edges 12a-12d of the core which can be undesirable as the coating can rupture during expansion which will result in water penetration in an uncontrolled manner and more rapid and uncontrolled expansion of the core 12 than may be desired. In order to overcome this problem, the present invention includes the step of forming the core material 12 with edges having a radius of curvature R and coating said coating 14 onto the core 12 by moulding said coating 14 around the core 12 and the step of forming the coating material 14 with edges 14e adjacent the edges 12e of the core and having a radii of curvature r which is less than the radii of curvature R of the edges of the core 12. A plurality of apertures 20, 22, 24 as discussed above are then provided through said coating 14. The coating 14 is preferably provided in the form of a water impermeable coating and the apertures 20, 22, 24 may be formed during the coating process.

The above-described manufacturing process provides an expandable implant 10 which may be used in medical and other procedures and which may be provided with both a delay before expansion and a controlled rate of expansion when initiated. Those skilled in the art will appreciate that the swelling pressure is provided by the hydration of the polymer network (e.g. xerogel) to form a fully swollen polymer network (e.g. a hydrogel) which occurs in vivo. The self-inflating polymer network is preferably a xerogel/hydrogel, i.e. the network changes from a xerogel to a hydrogel as it absorbs water in vivo. The self-inflating polymer network may preferably generates a swelling stress pressure of up tp 200 kPa1-50 kPa/cm2, and more preferably 2-20 kPa/cm2. The absolute swelling pressure may be up to 100 kPa and is preferably at least 30 kPa.

The invention claimed is:

1. A tissue expander comprising a self-inflating core having a non-inflated state and an inflated state and a coating surrounding said core, characterized in that said core comprises a compacted material having a central portion of a first, higher, (average) density D and a peripheral portion of a second, lower, (average) density d, a border between said central portion and said peripheral portion and wherein said coating includes a plurality of first and/or second apertures through said coating.

2. The tissue expander of claim 1, including the plurality of first apertures radially spaced from said border and radially inwards thereof.

3. The tissue expander of claim 1, including the plurality of second apertures positioned on said border.

4. The tissue expander of claim 1, including a plurality of third apertures radially spaced from said border and radially inwards thereof.

5. The tissue expander of claim 2, wherein said plurality of first apertures are circumferentially spaced around a central axis X of said tissue expander.

6. The tissue expander of claim 3, wherein said plurality of second apertures are circumferentially spaced around a central axis X of said tissue expander.

7. The tissue expander of claim 4, wherein said plurality of third apertures are circumferentially spaced around a central axis X of said tissue expander.

8. The tissue expander of claim 1, wherein said self-inflating core includes an upper surface and a lower surface and wherein the plurality of first and second apertures are provided through said coating adjacent to each of said upper and lower surfaces.

9. The tissue expander of claim 1, including a semi-permeable barrier material within one or more of said plurality of first apertures for controlling the rate of water ingress.

10. The tissue expander of claim 1, including a semi-permeable barrier material within one or more of said plurality of second apertures for controlling the rate of water ingress.

11. The tissue expander of claim 1, wherein said core includes edges and wherein said coating has a greater thickness (T) adjacent to said edges than at other portions.

12. The tissue expander of claim 1, wherein said core includes first edges having a radius of curvature R and wherein said coating has second edges adjacent to said first edges and having a radius of curvature r less than said first radius of curvature R.

13. The tissue expander of claim 1, wherein said core comprises a self-inflating polymer.

14. The tissue expander of claim 1, wherein said coating comprises a water impermeable coating.

15. A method of manufacturing the tissue expander of claim 1 comprising the steps of:
 a) selecting a self-inflating hydrophilic core material;
 b) forming said selected core material to a given height H and width W;
 c) compacting said core material with a force F sufficient to overcome slipping friction and reducing the height H thereof whilst increasing the width W thereof;
 d) compacting the central portion to the first, higher, (average) density D and the peripheral portion to the second, lower, (average) density d, and creating the border between said central portion and said peripheral portion;
 e) coating said core with the coating; and
 f) providing the plurality of first and/or second apertures through said coating;

wherein the force F required to overcome the slipping friction is determined from F=2k exp(2μ/h (b/2−x)); and wherein the force required to overcome the sticking friction is determined from the following formula:

$$F = 2k\left(1 + \left(\frac{\frac{b}{2}-x}{h}\right)\right)$$

Where: F=force, μ=friction, k=shear yield stress, h=height, b/2=radius and x=distance from center.

16. The method of claim 15, including the further steps of:
 a. partially hydrating said self-inflating hydrophilic core material between steps (a) and (b); and
 b. de-hydrating said self-inflating hydrophilic core material between steps (b) and (c).

17. The method of claim 15, including the step of forming the core with edges having a radius of curvature R and coating said coating onto the core by molding said coating around the core.

18. The method of claim 15, including the step of forming the coating with edges adjacent to the edges of the core and having a radii of curvature r which is less than the radii of curvature R of the edges of the core.

19. The method of claim 15, including the step of providing the coating in the form of a water impermeable coating.

20. The method of claim 15, including the further steps of providing a semi-permeable coating within one or more of the plurality of the first and/or second apertures through said coating.

* * * * *